United States Patent [19]

Brunsch et al.

[11] Patent Number: 4,785,239

[45] Date of Patent: Nov. 15, 1988

[54] METHOD AND APPARATUS FOR CHARACTERIZING MAGNETIC COATING COMPOSITIONS AS WELL AS IMPROVING MAGNETIC PARTICLE DISPERSIONS

[75] Inventors: Arwed Brunsch, Stuttgart; Werner Steiner, Boblingen; Gerhard Trippel, Sindelfingen, all of Fed. Rep. of Germany

[73] Assignee: International Business Machines Corporation, Armonk, N.Y.

[21] Appl. No.: 871,969

[22] Filed: Jun. 9, 1986

[30] Foreign Application Priority Data

Jun. 13, 1985 [EP] European Pat. Off. ........ 85107346.0

[51] Int. Cl.⁴ ..................... G01N 27/74; G01R 33/12; B05D 5/12
[52] U.S. Cl. ..................................... 324/204; 427/130
[58] Field of Search ............... 324/204, 232, 306, 319; 427/48, 47, 128, 130

[56] References Cited

U.S. PATENT DOCUMENTS 2,215,605  9/1940  DeLenty .............................. 324/225
2,894,199  7/1959  Kirchner ............................. 324/319
3,001,891  9/1961  Stoller ................................. 427/48
4,651,092  3/1987  Brunsch et al. ..................... 324/204

Primary Examiner—Reinhard J. Eisenzopf
Assistant Examiner—Alter E. Snow
Attorney, Agent, or Firm—Homer L. Knearl

[57] ABSTRACT

A method and apparatus is provided for characterizing magnetic coating compositions that contain magnetic particles dispersed in a solvent resin matrix. The coating composition, as it passes through a tube, is subjected to an alternating magnetic field and perpendicular thereto a constant magnetic field of appropriate field strength and duration. Via a measuring coil surrounding the tube the induced signal in the composition is monitored and the degree of dispersion, is measured by measuring the magnetic susceptibility of the coating material. By applying a constant magnetic field the degree of dispersion cna be changed at least for a certain time. The method and apparatus of the present invention can be incorporated into a coating apparatus to monitor and improve the magnetic characteristics of the coating material being applied to a substrate.

11 Claims, 7 Drawing Sheets

V

VI

VII

VIII

METHOD AND APPARATUS FOR CHARACTERIZING MAGNETIC COATING COMPOSITIONS AS WELL AS IMPROVING MAGNETIC PARTICLE DISPERSIONS

FIELD OF THE INVENTION

The present invention relates to a method and apparatus for characterizing magnetic coating compositions of a dispersion of magnetic particles in a fluid resin solvent mixture. Furthermore the present invention relates to a method and apparatus for improving magnetic particle dispersions.

BACKGROUND OF THE INVENTION

Magnetic coating compositions containing magnetic particles, such as $\gamma$-$Fe_2O_3$ pigment, are widely used for producing magnetic record carriers, in particular, magnetic disks and magnetic tapes. After the application of the magnetic coating composition onto the carrier, the majority of the solvent evaporates. During or after the application of the coating composition and the evaporation of the solvent, there takes place an orientation of the magnetic particles, the curing and polishing of the record carrier, if necessary a lubrication of the surface, and finally a test for the magnetic characteristics of the record carrier. The quality of the magnetic coating composition is of decisive importance for the quality of the magnetic record carrier.

The magnetic coating composition is generally made by using methods of paint production. Apart from precisely observing the chemical composition, it is of great importance to implement a complicated mechanical processing, for example ball milling the coating material to disperse the magnetic particles within the resin solvent fluid as good as possible. This, and the physical-chemical characteristics of the components of the coating composition, as well as their interaction, determine the internal structure of the coating composition, with the degree of dispersion and of agglomeration of the individual particles playing an important part.

For these characteristics which strongly influence the quality of the finished record carrier there do not yet exist any direct measuring means. The viscosity of the coating composition which very much depends on the internal structure influences the processing characteristics. Electrostatic and magnetostatic forces between the magnetic particles can cause aging which only becomes visible later in the finished record carrier.

The quality of the coating composition is at present mostly tested in production in that a control record carrier is made which substantially corresponds to a finished record carrier, and that the latter is then tested for quality. Further use of the coating composition depends on this check. It is obvious that such a test is very time-consuming, expensive and imprecise since immediately before, and during the application of the coating composition onto the carrier, no measure of the quality of the coating composition is available.

Decisive factors for the quality of the magnetic coating composition are the degree of dispersion or of agglomeration, respectively, the particle density, and the viscosity. Furthermore, the stability of the composition place a part which strongly depends on time, i.e., what is the stability of the coating composition during a predetermined period or in other words, does the coating composition age prematurely, and if so, to what extent?

In Applicant's co-pending patent application Ser. No. 534,471 Filing Date Sept. 21, 1983, now U.S. Pat. No. 4,651,092, a method and an arrangement is described for characterizing magnetic coating compositions consisting of a dispersion of magnetic particles, particularly $\gamma$-$Fe_2O_3$ pigment, in a liquid resin-solvent mixture. In accordance with this known solution the coating composition is exposed to an alternating magnetic field of variable frequency, the signal induced by the alternating magnetic field is received from the coating composition, and consequently the susceptibility thereof is measured as a factor of the variable frequency, and evaluated with respect to the degree of dispersion, the particle density, and to the viscosity of the coating composition. This known method and apparatus allows the measuring and controlling of the quality of the coating composition.

Nevertheless this known method and arrangement is somewhat limited in its measuring flexibility. It is not possible to change the composition during measurement for measurement purposes and therefore also it is not possible to change the degree of dispersion even for a very limited period of time.

SUMMARY OF THE INVENTION

It is therefore an object of the present invention to improve the known measuring method and arrangement, so that more exact measuring results with a wider variety of evaluation possibilities are given. At least for measuring purposes there should be the capability of changing the magnetic characteristics of the magnetic coating composition. It is furthermore an object of the present invention to provide a method and an apparatus for improving the degree of dispersion of a magnetic coating composition as well as maintaining this improved degree of dispersion.

In the present invention, this object is achieved in that during measurement and exposure to an alternating magnetic field the coating composition is exposed to a constant magnetic field whose direction is perpendicular to the direction of the alternating magnetic field and that the constant magnetic field is of an appropriate duration and field strength that a remarkable change in the measured induced signal is detectable.

The advantages of the invention are the ability to measure the magnetic susceptibility of the composition to gain direct values that express the degree of dispersion and other characteristics of the magnetic composition. Also based on the measuring method, a method is provided that in an advantageous manner allows improvement in the degree of dispersion and a way to maintain that improved degree of dispersion.

The apparatus for measuring the magnetic characteristics of the coating composition can in advantageous manner be used to improve the degree of dispersion as well as to monitor and measure this improved degree of dispersion. If the apparatus for measuring is incorporated into a coating station in which magnetic record carriers are produced by applying the coating composition onto substrates, then a highly advantageous integrated processing apparatus for producing record carriers is implemented.

DESCRIPTION

The invention will be described in detail with reference to a drawing which merely represents one preferred embodiment. The figures depict the following:

FIG. 1 schematically shows a basic arrangement of coils for generating and measuring the different fields in accordance with the inventive method.

FIG. 2 shows the magnetic behavior of magnetic particles subjected to an alternating magnetic field as well as induced signals.

FIG. 3 schematically shows the magnetic behavior of magnetic particles subjected to an alternating magnetic field and in addition thereto to a pulse-like constant magnetic field in accordance with the present invention, as well as induced signals.

Figure 1:
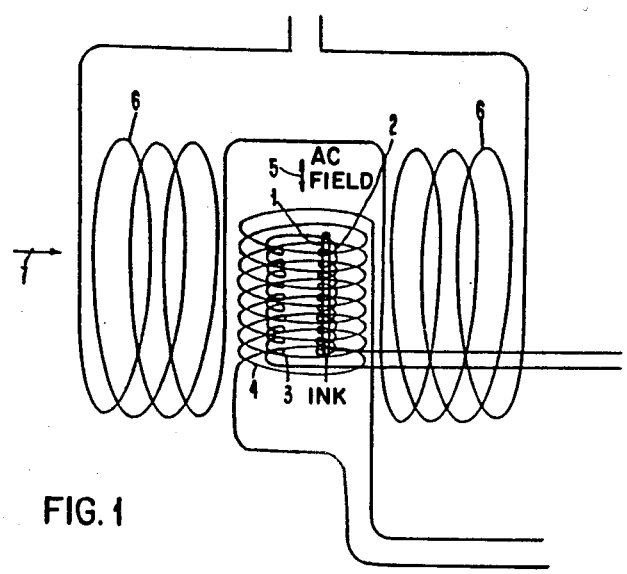

Magnetic liquid coating compositions or paints or inks respectively that are used in the manufacturing of magnetic record carriers such as disks or tapes consists essentially of magnetic single domain particles such as for example $\gamma$-$Fe_2O_3$, dispersed more or less stably in a liquid binder matrix. The magnetic performance of such a particle assembly depends on the perfectness and on the stability of the dispersion. The perfectness of the degree of dispersion or dispersion grade respectively and the stability of the dispersion is determined by both, the ink preparation process and by the physical-chemical interactions of the ink components. As gravitational, electrostatic and magnetostatic forces and interactions between the particles cause pronounced alterations with time, the control of the dispersion condition of a magnetic liquid ink is always an intricate task. Therefore a method to quantitatively determine the dispersion condition of an ink and related properties such as dispersibility, dispersion stability, orientation order is beneficial in order to control the manufacturing process of magnetic recording carriers such as disks and tapes.

In case of magnetic pigments it is rather natural to think of magnetic measurements in order to get information about the microscopic structure of a particle assembly. The method and arrangement in accordance with the present invention, called DIMAG—DIspersion by MAGnetic measurement—is a method and a tester to reveal information about the structural arrangement of the particles themselves, the dynamic processes caused by internal interactions, and the influence of external magnetic fields. The application of those external felds is effective to disperse loosely agglomerated particle assemblies. Thus the concept of the DIMAG is apt for analysis purposes as well as for improving the dispersion process and for maintaining an improved dispersion.

As the term "dispersion" is poorly defined, an attempt is made to formulate a physical definition of the term "dispersion" and related properties. In this definition dispersion refers to the arrangement of nearest neighbors rather than to the occurrence of agglomerates or clumps. Thus the physical significance of the data obtained by the DIMAG differs from commercially available dispersion monitors that are essentially clump detectors.

The DIMAG tester in accordance with the invention is a device to sense the dispersion condition of a magnetic coating ink by measuring its magnetic susceptibility. The method essentially consists of a time limited application of a constant magnetic field perpendicular to an applied alternating field, whereby the application of the constant magnetic field changes the signal response due to the alternating magnetic field in a manner which is characteristic to the dispersion condition of the magnetic composition. The characteristic differences which can be observed include chemical differences of inks of different qualities as well as differences in the preparation process. Thus the DIMAG is suited to monitor inadvertent differences in the quality of coating ink batches.

DC pulses of varying field strength, those pulses forming the time limited constant magnetic field, lead to irreversible changes in the magnetic characteristics of the ink. These responses to magnetic fields can be interpreted in a semi-quantitative way. Also the understanding is by no means complete, it has led to subtle insight into the microstructure of a dispersion of magnetic particles. Besides the DIMAG's use as an analytic tool, a potential additional application is the active support of the dispersion process by magnetostatically separating agglomerated particles. The rate at which the separation occurs and the rate of reagglomeration can be observed simultaneously.

Referring now to FIG. 1, the preferred arrangement of coils to realize the DIMAG method is shown. The ink to be measured and monitored is contained within a non-magnetic and non-conductive tube 1, for example, a glass or plastic pipe, vessel or test-tube. The vessel 1 is surrounded by a measuring coil 2 to measure the induced signal. Parallel to coil 2 an empty compensation coil 3 is provided. This compensation coil 3 is mechanically and electrically identical with the measuring coil 2 and connected in a compensating mode, i.e., electrical opposition. Both coils 2 and 3 are surrounded by a coil 4 which generates an energizing alternating magnetic field, the AC field in direction of double arrow 5. The AC field oscillates in direction of the longitudinal axis of tube 1 and measuring coil 2.

In accordance with the method of the present invention a constant magnetic field is applied perpendicularly to the AC field. The application of this constant magnetic field is performed for a certain duration and with a certain field strength. To this end a two-part coil 6 is provided on both sides of the AC field coil 4 to apply the DC field in the direction of arrow 7.

The frequency of the energizing alternating AC field might be between 10 and 100 hz and is chosen to be preferably about 80 hz. The field strength of the alternating magnetic field is between 10 and 100 oerstedts and chosen to be preferably about 35 oerstedts.

The duration of the constant magnetic field, the DC field pulse length corresponds essentially at least to the relaxation time of the physical magnetic particle motion within the liquid binder material. As used herein, relaxation time is the minimal time needed in a given binder system to turn a single particle into alignment with the DC field. In practical examples the duration of the DC field pulse is between 1 and 60 seconds and preferably about 10 seconds. The field strength of the DC field pulse depends on the material to be tested and influenced. There exists a critical field strength which in most cases for standard inks coincides approximately with the coercive field strength of that respective material.

Figure 2:
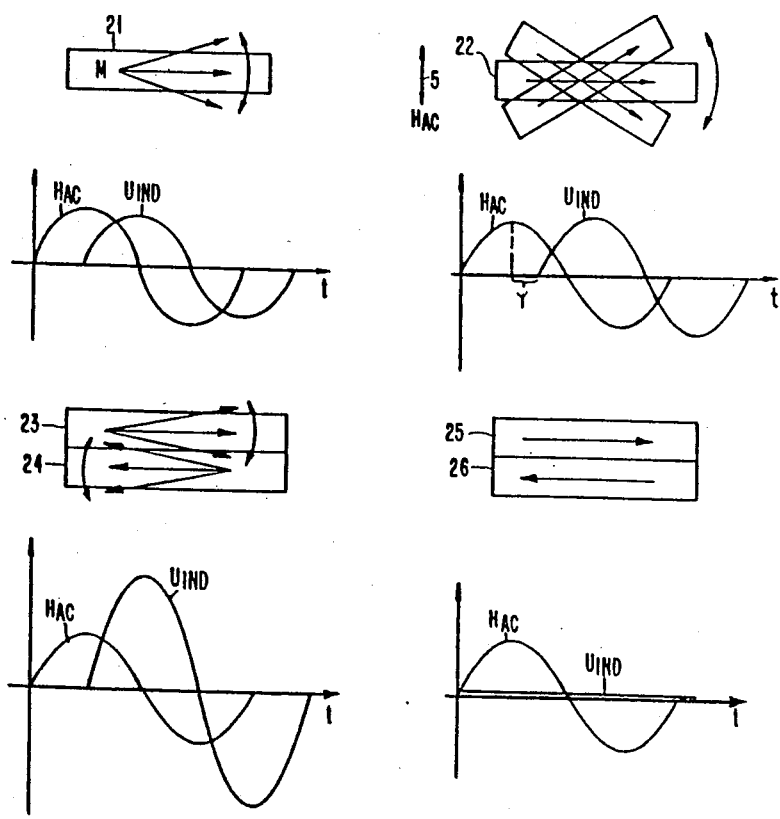

With reference to FIG. 2, there is shown in the left half the change of the direction of magnetization within a single particle and in the right half the position change of a single magnetic particle under the influence of the energizing magnetic alternating field $H_{AC}$ along double arrow 5. In the upper left half of FIG. 2 a single magnetic particle 21 is shown whose direction of magnetization within the particle is perpendicular to the direction 5 of the alternating field $H_{AC}$. It is assumed that particle 21 is physically in a stable position. The magnetization within the particle oscillates around the equilibrium axis by the influence of the alternating field $H_{AC}$. Such a tilt for the equilibrium axis of the magnetization can only occur when the alternating field is applied perpendicular to the magnetization M within the particle 21. This magnetization process is very fast compared to the applied frequency of 80 hz.

The diagram underneath magnetic particle 21 shows one cycle of the alternating field $H_{AC}$ and the induced signal $U_{IND}$ in measuring coil 2. Magnetization within magnetic particle 21 oscillates together with the applied frequency and direction of the energizing alternating magnetic field $H_{AC}$. Therefore, the included signal voltage is proportional to the frequency and to the applied field. As long as the magnetization process is fast, i.e., the frequency is small compared to the relaxation time, there is a phase shift of the signal amplitude $U_{IND}$ to the applied field of 90 degrees. The amplitude of the applied alternating field controls the strength of oscillation of the magnitization in magnetic particle 21 and therewith the amplitude of the induced signal $U_{IND}$. Compared to agglomerates single particles induce a high signal amplitude.

In the upper right corner of FIG. 2 a magnetic particle 22 is shown under the influence of a vertically applied magnetic field $H_{AC}$. This particle suspended in a viscous binder matrix experiences a mechanical torque when the field $H_{AC}$ is oriented perpendicularly to the particle axis. This leads to a physical oscillation of the particle. In a viscous matrix this is a slow process. Therefore, a phase lag $p$ between oscillation indicated by the induced signal $U_{IND}$ and the applied and energizing magnetic alternating field $H_{AC}$ can be expected. The diagram shows this phase lag between a cycle of $H_{AC}$ and the coil 2 induced signal $U_{IND}$ as function of time t.

In the lower left corner of FIG. 2 a pair of particles 23 and 24 is depicted whose magnetization direction is opposite to each other. The diagram underneath this particle pair shows that the induced signal $U_{IND}$ is twice the amount of the induced signal of the situation with particle 21 above in the upper left corner of FIG. 2. This means that the signal induced due to the internal magnetization is doubled.

In the lower right corner of FIG. 2 a pair of magnetic particles 25 and 26 is depicted whose magnetization direction is also opposite to each other. There is no position change by this pair in the presence of the alternating field $H_{AC}$. The induced signal $U_{IND}$ under the influence of a perpendicularly applied magnetic alternating field $H_{AC}$ is zero as far as the position change due to the applied alternating field is concerned.

The signal change due to the direction of magnetization within the particle in the induced signal does not depend on the dispersion grade. This dependency is shown in the left half of FIG. 2. In the right half of FIG. 2 the change due to position change under the influence of the applied alternating magnetic field $H_{AC}$ shows that the induced signal is depending on the dispersion grade. Only single particles contribute in this example to the induced signal. The pair 25 and 26 does not contribute to the induced signal $U_{IND}$.

Figure 3:
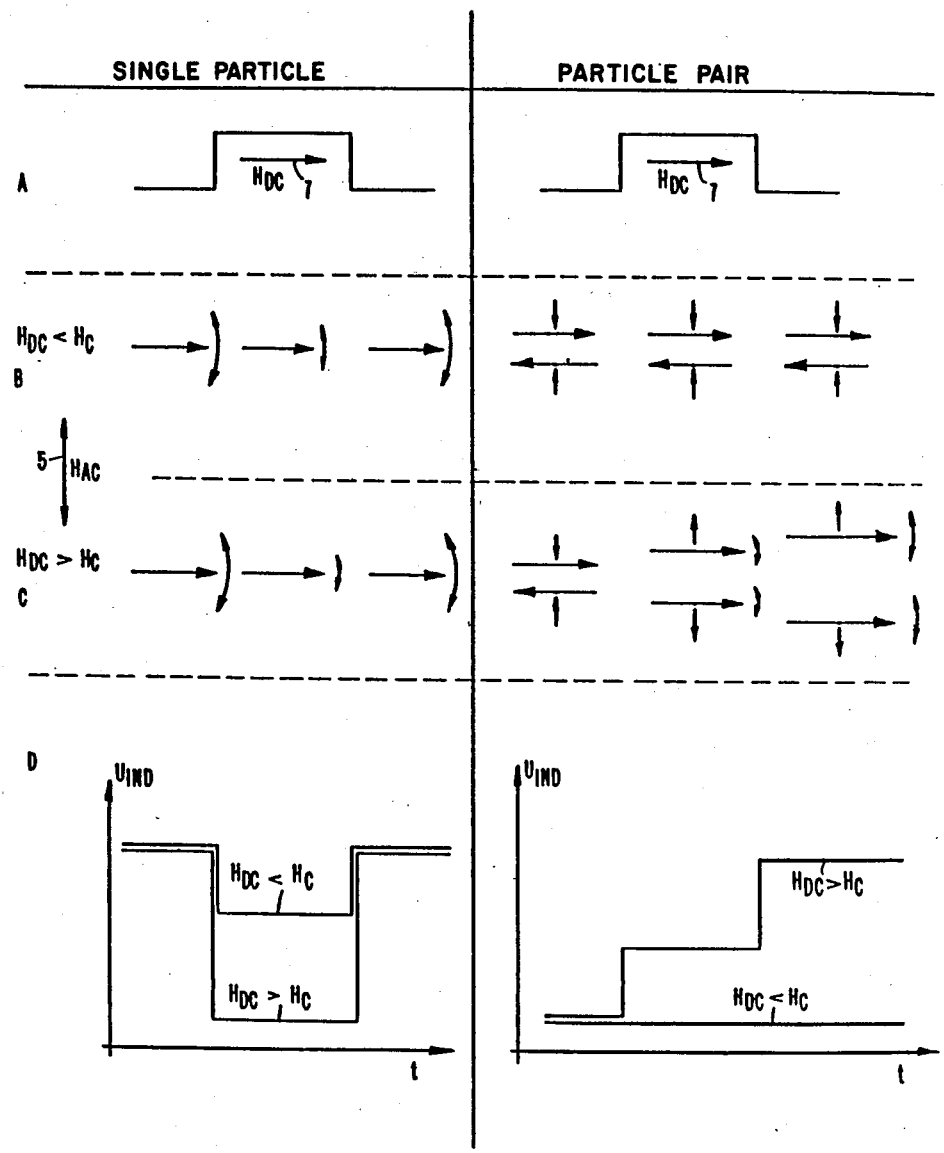

With reference to FIG. 3 the magnetic behavior of a single magnetic particle in contrast to a particle pair, both subjected to an alternating magnetic field and in addition thereto to a pulse-like constant magnetic field orthogonal to the alternating field will be discussed. The left half of FIG. 3 deals with the case for a single particle whereas the right half of FIG. 3 deals with a particle pair.

The effect of a magnetic constant field, applied as a DC pulse, orthogonal to an alternating field $H_{AC}$, acting in direction of arrow 5, on the AC signal particle response producing the induced signal $U_{IND}$ depends on the agglomeration state of the particles. The response of interacting particles will be outlined qualitatively for a single particle and particle pairs. In this model only pair interaction is being considered and thus the results only indicate the principal qualitative behavior. Thus the difference between the two cases is discussed in parallel.

The applied alternating field $H_{AC}$ is perpendicular to the applied constant field $H_{DC}$ as indicated by the two arrows 5 and 7. Line A indicates the constant magnetic field applied in the form of a DC pulse $H_{DC}$. Line B indicates the two cases (single and pair) where the field strength of the applied constant field $H_{DC}$ is smaller than the coercive field strength, or coercivity, $H_C$ of the material, $H_{DC} < H_C$. Line C indicates the cases where the field strength of the applied constant magnetic field is greater than the coercive field strength, $H_{DC} > H_C$. In Line D the two cases of the induced signal $U_{IND}$ are depicted over the time t for both $H_{DC}$ strengths.

In each case shown in the left half and the right half of FIG. 3 as well as in the cases of the different field strength the response of the particles to the AC field before, during and after the application of the constant magnetic field pulse $H_{DC}$ and their spatial arrangement is shown.

In accordance with line B right half where particle pairs in the indicated arrangement form a magnetostatically stable configuration, the net magnetic moment is zero. Thus a weak magnetic alternating field does not cause the particle to oscillate. No contribution to the signal is expected apart from the orientation of the pair. This is the case when the applied constant magnetic field is lower than the critical magnetic field strength $H_C$.

As shown in line B left half a single particle whose magnetization is parallel to the constant magnetic field generates a maximum signal $U_{IND}$. This induced signal $U_{IND}$ decreases during application of the constant magnetic field $H_{DC}$. After switching off this constant magnetic field the induced signal $U_{IND}$ will revert to its original value. This response to a DC field pulse $H_{DC}$ is instantaneous. Particles whose magnetization have a finite angle to the constant magnetic field direction 7 will be rotated by this field until they are aligned in the direction of the field. Thus the signal response to the orthogonal alternating field $H_{AC}$ will slowly increase. The rate of increase depends on the viscosity and on the texture or orientation order respectively. In a partially ordered system of particles the orientation is a coordinated process which takes less energy than in a completely disordered assembly of particles where the neighboring particles impede each other. The physical rotation of the particles is a slow process. Its relaxation time is in the order of the DC pulse length of about 10 seconds.

Now the right part of line C in FIG. 3 is explained. In this case of a particle pair to which a DC pulse is applied whose field strength is greater than a critical value $H_C$, which is the coercivity of the particle. Those particles in pairs which particles are magnetized opposite to the direction 7 of the constant field pulse $H_{DC}$ will be magnetically switched. The attractive force between the pair switches to a repellent force which causes the particle pair to separate. Thus the application of strong constant fields leads to magnetic dispersion of particle assemblies. As the particle pair is separated, the now created two single particles contribute to the signal response $U_{IND}$. An abrupt increase of the signal $U_{IND}$ can be expected and is depicted in the lower right part of FIG. 3. This is actually observed experimentally.

In the presence of a constant magnetic field singular particles will form a particle chain which reduces the magnetostatic energy. As a result, for example depicted in line C left part of FIG. 3 and the induced signal in line D left half of FIG. 3, the free movement of the particles that means their oscillation is reduced and therewith the induced signal $U_{IND}$.

Figure 4A:
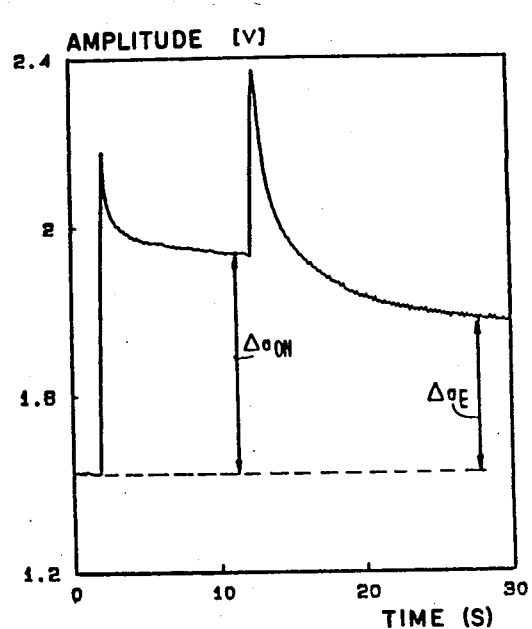
FIGS. 4A and 4B are diagrams of the induced signal amplitude and phase over the time of application of the different magnetic fields.
Figure 4B:
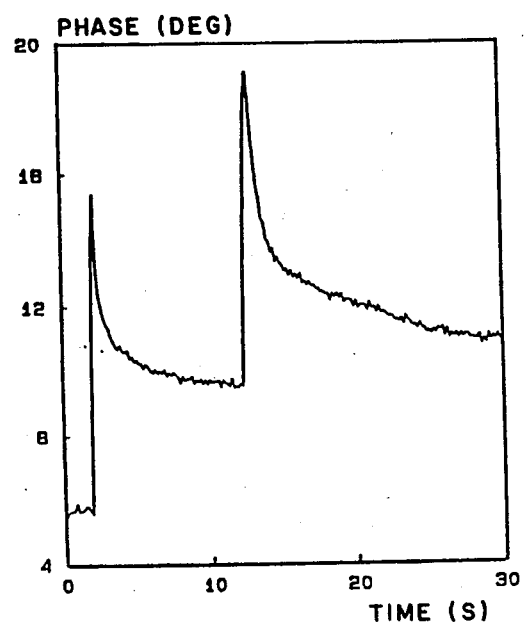

In FIGS. 4A and 4B the amplitude and the phase are depicted versus the time for the measurement of a standard ink. The diagram shows the induced signal amplitude and the phase over time during the application of the different magnetic fields. The shown measuring cycle incorporates a time period of 30 seconds. The frequency of the alternating magnetic field is 80 hz and its field strength is about 36 oerstedts. The field strength of the constant magnetic field is 475 oerstedts.

At time point zero the alternating field is applied to the coil 4 and a certain start value for the amplitude about 1.4 Volts and the phase is reached. After about 2 seconds the constant magnetic field is switched on. An immediate increase of the induced signal amplitude and a change in the phase is observed. This is due to a spontaneous creation of single particles. After the abrupt increase of the induced signal after the constant magnetic field is turned on, a relative slow decrease of the signal amplitude as well as the phase value occurs. This slow decrease is contributed by the chain forming.

After about 12 seconds the DC pulse forming the constant magnetic field is turned off, and there is an immediate increase in amplitude and phase value. This increase is contributed by removal of the magnetic damping forces due to the DC field and the magnetic damping forces acting on chains. The DC field dampens movement of the particles caused by the AC field. The amplitude and also the phase values decrease after the turn off of the DC pulse. This is contributed by agglomeration or flocculation of particles to their magnetostatically most stable pair configuration. Therefore a slow decrease of the signal can be observed to the end of the measuring cycle at 30 seconds, when also the alternating field is turned off, and the measuring cycle is therewith terminated.

As FIGS. 4A and 4B show clearly, for a standard ink the application of a DC pulse forming a constant magnetic field of appropriate field strength and duration, changes the magnetic characteristics of the respective ink by increasing in two steps the signal amplitude induced under an applied alternating magnetic field as well as the phase value.

The microprocesses during and after the application of the pulse-like constant magnetic field, as outlined above, can be assumed to take place for larger particle assemblies in an equivalent manner. Nevertheless it should be noted that this model only represents a rough qualitative picture since the complex magnetostatic interactions were reduced to next neighbor interactions. The role of orientation order is completely neglected, nonetheless the various microprocesses can be distinguished and be rated quantitatively. This offers an opportunity to distinguish between the qualities of different inks.

Figure 5:
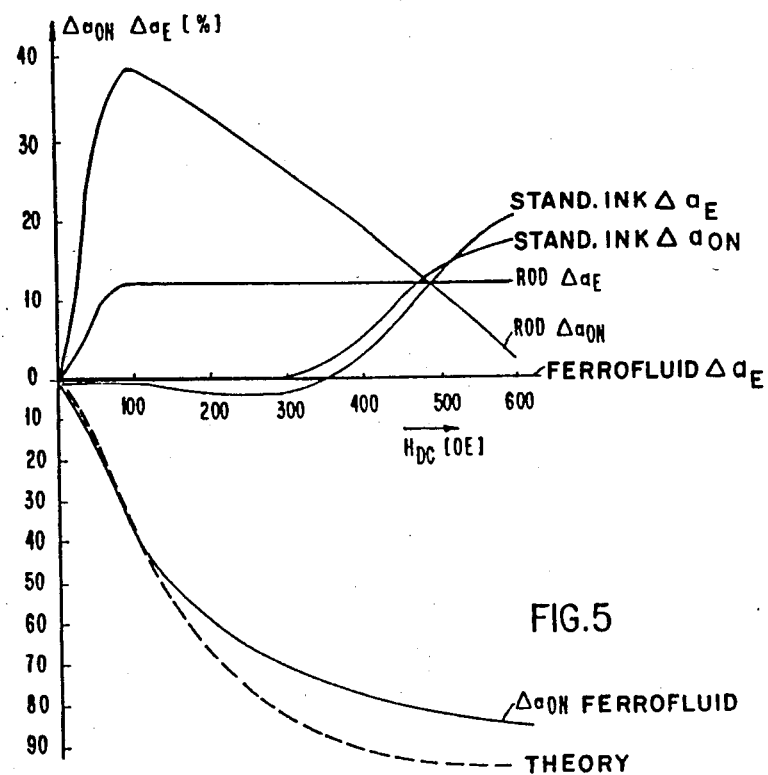
FIG. 5 is a diagram of the change of the induced signal for different magnetic compositions dependent on the field strength of the constant field.

Reference is made now to FIG. 5 that shows a diagram of the signal change over the field strength of the applied constant magnetic field pulse (DC pulse) for three different magnetic compositions. The signal change $\Delta a_{ON}$ is the change in percentage during the application of the DC pulse and the signal change $\Delta a_E$ is the remaining signal change after the DC pulse has been switched off. One material shown is ferrofluid. This is a magnetic dispersion that can be considered to be more or less an ideal dispersion. Therefore the curve for $\Delta a_{ON}$ of ferrofluid for different values of the constant magnetic field strength nearly follows the theory that means that all the single particles are increasingly damped with increasing field strength. That means in other words all or almost all the single particles are hindered to oscillate during the application of the constant field. After switching off the DC pulse, the value for $\Delta a_E$ is zero for ferrofluid that means there is no change to be observed because no dispersion improvement takes place with this material as it is already the ideal dispersion.

The second material shown in the diagram of FIG. 5 is the standard ink. This normal standard coating material has a limited dispersion grade which cannot be improved due to technical deficiencies. That means in other words there are quite a lot of agglomerates in the coating composition. To increase in the $\Delta a_{ON}$ value as well as in the $\Delta a_E$ value requires a large field strength for the applied constant field. A remarkable change for both values starts with about 400 oerstedts. A 20% increase is reached with 600 oerstedts field strength for the constant field.

A third material shown in the diagram of FIG. 5 is the so-called ROD coating material. This is an organic dispersion material containing $\gamma$-$FE_2O_3$ needlelike particles of about 1 μm thickness that are coated by an organic material. This organic material coating of the single particles avoids to a certain degree agglomeration of particles. Therefore the dispersion degree of such a material is higher than that of standard ink. With relatively low field strength, a high $\Delta a_{ON}$ value is reached. This $\Delta a_{ON}$ value decreases with increasing field strength for the DC pulse. The $\Delta a_E$ value reaches a nearly constant value with a field strength of 100 oerstedts and then remains essentially constant.

Figure 6:
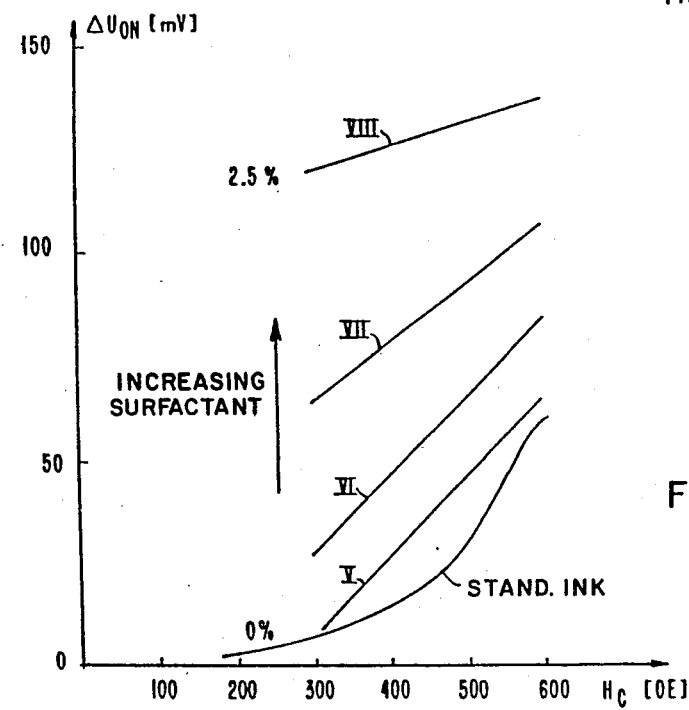
FIG. 6 is a diagram of the change of the induced signal for different magnetic compositions dependent on the field strength of the constant magnetic field.

Now reference is made to FIG. 6 wherein a diagram is depicted that shows the signal change of the induced signal $\Delta U_{ON}$ for different magnetic compositions dependent on the field strength of the constant magnetic field pulse, the DC pulse. The lowest curve shows the signal changes of a standard ink in dependency on the different field strengths. The highest change is produced with a field strength of about 600 oerstedts. Above this line four different materials are depicted that pertain to an ink that is improved as far as the dispersion grade is concerned. Those four different materials include an ink with a surfactant, an organic coating of the single particles, and an increasing portion of surface surfactant up to 2.5% of the millbase (0.6% of the magnetic coating composition) for the uppermost one. There is shown the tendency between the materials V, VI, VII and VIII for the values of field strength 300 oerstedts and 600 oerstedts. It is obvious that the material VIII with a 2.5% surfactant content (in practice means the complete surface of all particles is covered with the surfactant material), has with a field strength of 300 oerstedts an enormous signal increase which is not much less than the signal increase with 600 oerstedts. This material can be considered to be well or nearly ideally dispersed.

Figure 7:
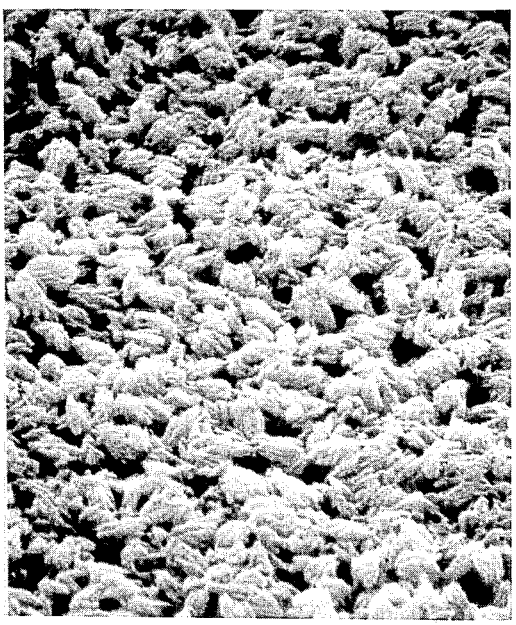
FIG. 7 shows enlarged microscopic pictures of the magnetic particle structure of four different magnetic compositions whose signal response is shown in FIG. 6.
Figure 7:
Figure 7:
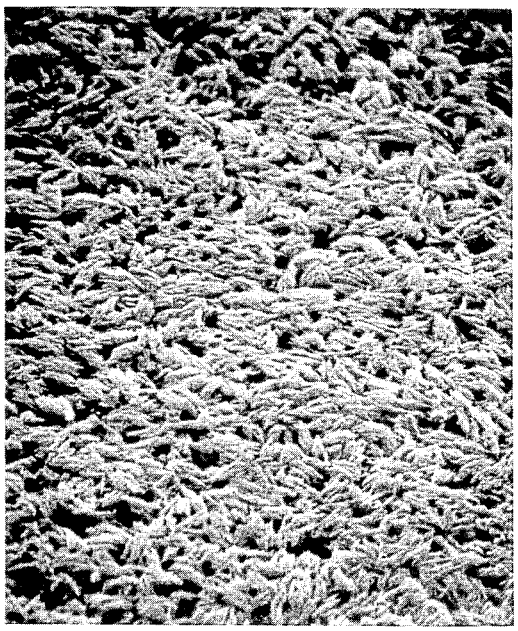
Figure 7:
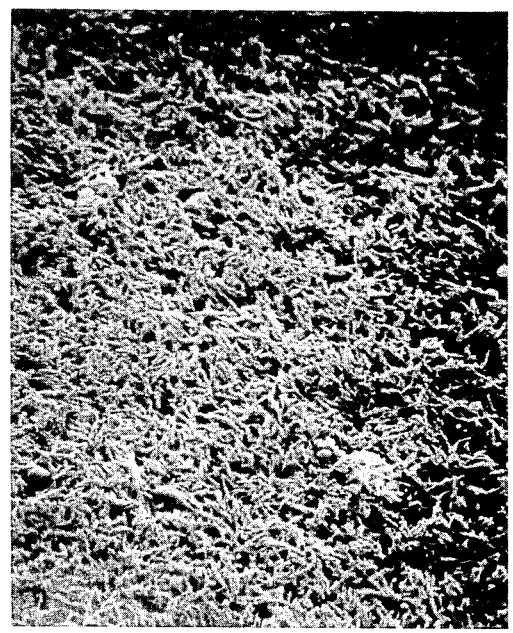

Reference is made to FIG. 7 which shows pictures of a scanning electron microscope of the magnetic particles of the four different materials V to VIII that were shown in FIG. 6. It is clearly visible that material V can be considered to be rough dispersed and material VIII can be considered to be fine dispersed. Thus the magnetic particles are best distributed and each area of a record carrier is best provided with magnetic material if a dispersion like the one shown within material VIII is used.

Figure 8:
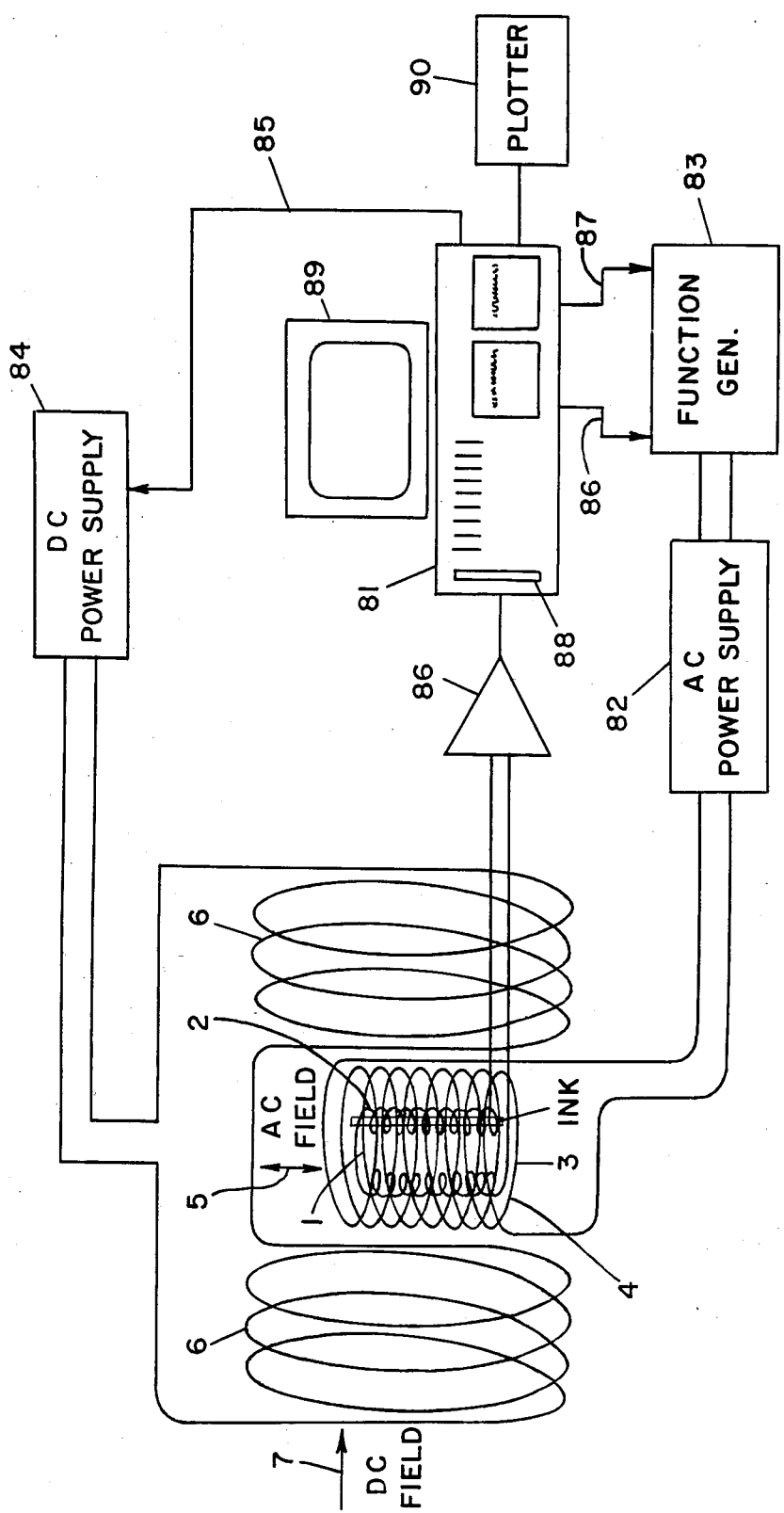
FIG. 8 is a block diagram of the measuring arrangement in accordance with the present invention.

Reference is made to FIG. 8 in which in a block diagram the measuring arrangement in accordance with the present invention is depicted. The DIMAG essentially consists as already shown in FIG. 1 of the arrangement of different coils. The ink to be measured is contained in tube or conduit 1 surrounded by measuring coil 2. Connected with measuring coil 2 is an identical compensating coil 3. Both coils are connected to a preamplifier 80 that feeds into a control unit 81. The measuring coil 2 and the compensating coil 3 are surrounded by the AC field coil 4. AC field coil 4 is connected to an AC power supply 82 which in turn is controlled by a function generator 83.

For generating the magnetic constant DC field a Helmholz coil pair 6 is provided orthogonal to the AC field coil 4. The DC field coil 6 is supplied by a DC power supply 84 which in turn is set in regard to field strength and pulse time by signal on line 85 from the control unit 81. Control unit 81 in turn triggers over line 86 the function generator 83 and also sets over line 87 the AC frequency and the AC amplitude of the function generator.

The signal induced in measuring coil 2 by the AC field under the influence of the DC field and amplified in the preamplifier 80 is fed via an analog-digital conversion card 88 to the control unit 81. In accordance with a preferred embodiment of the invention control unit 81 is realized by an IBM Personal Computer. Thus the whole measuring cycle as well as the evaluating and computing of the measuring results can be programmed and automatically performed. Results can be printed on an output printer, can be displayed on screen 89 and/or plotted on a plotter 90.

The values for the set field strength for the constant magnetic field might vary between 50 and 625 oerstedts and the pulse length corresponds essentially to the relaxation time of the magnetic material. Depending on the material this relaxation time might vary between 2 and 60 seconds and preferably is about 10 seconds. The AC field frequency was set to 80 hz but might vary between 10 and 100 hz and the AC amplitude of field strength respectively was adjusted to 36 oerstedts as a preferred value but might vary between 10 and 100 oerstedts.

Figure 9:
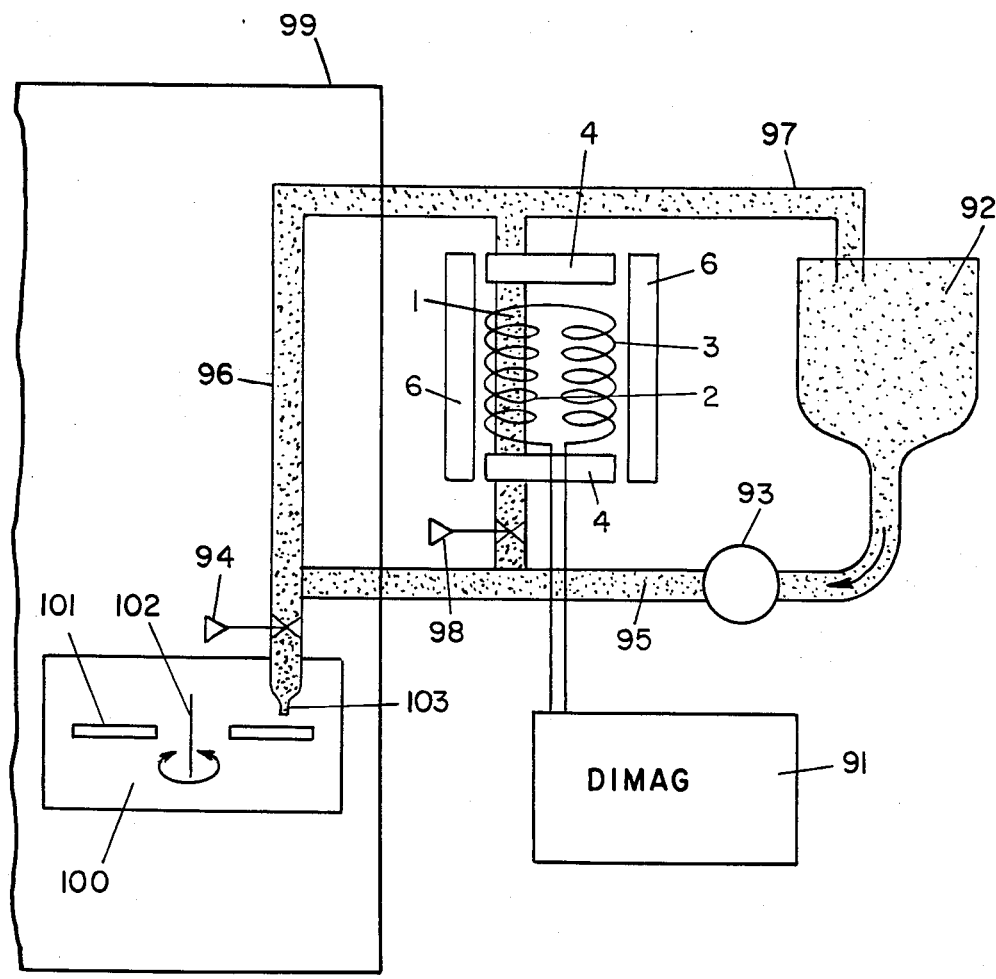
FIG. 9 is a block diagram of the device in accordance with the present invention incorporated in an in-line system of a coating station for producing magnetic disks.

Reference is made now to FIG. 9 in which the DIMAG is shown in an in-line system together with a coating system. The DIMAG system 91 incorporating essentially the control unit, the function generator, the power supplies and evaluation input/output devices is connected to the sense or measuring coil 2 via the compensation coil 3. The AC field coil 4 and the DC field coil 6 are shown schematically without connection lines. The tubular member 1 that contains the ink to be measured and treated forms part of a pipe system within that coating station. From a reservoir 92 a pump 93 pumps coating material to a nozzle 103 if a control valve 94 is opened. If control valve 94 is closed the material is pumped by pump 93 via pipe 95 over pipes 96 and 97 back to reservoir 92.

Through control valve 98 a bypass around pipe 96 can be opened through tube 1 between pipe 95 and 97. Thus pump 93 can pump coating ink through this tubular member. The ink contained in the section of pipe-like part 1 that is surrounded by measuring coil 2 and the coils that generate the different magnetic fields, is subjected to those fields and treated in accordance with the method of the present invention. Thus the dispersion grade is measured and the dispersion itself can be improved. It is also possible to maintain a certain degree of dispersion in the ink.

Thus the coating material is successively subjected to that procedure and this procedure is repeated to continuously improve the dispersion grade and to maintain it at a high level.

The coating station indicated by reference number 99 includes a coating chamber 100 in which or example a magnetic disk substrate 101 rotates around an axis 102 while ink is applied through nozzle 103 when control valve 94 is opened. The ink supplied on disk substrate 101 preferably has the highest degree of dispersion possible by treatment and supervision of the DIMAG 91 and its associated parts.

Thus the arrangement schematically shown in FIG. 9 might be used for measuring and characterizing the used magnetic coating material as well as improving the degree of dispersion of said material and at the same time measuring this improvement and the status of the maintained dispersion.

Thus the method of the present invention and the apparatus for implementing this method serve in an advantageous manner to characterize magnetic coating material as well as improve its characteristics. Therefore improved magnetic record carriers can be produced.

While we have illustrated and described the preferred embodiments of our invention, it is understood that we do not limit ourselves to the precise constructions herein disclosed, and the right is reserved to all changes and modifications coming within the scope of the invention as defined in the appended claims.

We claim:
1. A method for characterizing magnetic coating compositions having a dispersion of magnetic particles in a fluid resin solvent mixture, comprising the steps of:
   exposing said coating composition to an alternating magnetic field;
   exposing said coating composition to a constant magnetic field during exposure to said alternating magnetic field, said constant magnetic field is applied perpendicular to the direction of said alternating magnetic field for a portion of a measurement interval and is of a field strength greater than the coercive field strength of the magnetic particles;

said portion of the measurement interval is at least as great as the relaxation time of the magnetic particles in the fluid resin solvent;

detecting the signal induced by magnetic field changes in said coating composition when exposed to said alternating magnetic field before, during and after simultaneous exposure to said constant magnetic field;

measuring characteristics such as degree of dispersion and particle density of said coating composition from said induced signal.

2. Method of claim 1 wherein:

said measuring step measures the response of said magnetic particles to said alternating magnetic field before, during and after exposure to said constant magnetic field, as well as the effect of said constant magnetic field on the spatial arrangement of said particles.

3. Method of claim 2 wherein:

the strength of said alternating magnetic field is between 10 to 100 oerstedts.

4. Method of claim 3 wherein:

the frequency of said alternating magnetic field is between 10 and 100 hz.

5. Method for improving the degree of dispersion of a magnetic coating composition consisting of a dispersion of magnetic particles in a liquid resin solvent mixture comprising the steps of:

exposing said magnetic coating composition to an alternating magnetic field;

exposing said coating composition, in addition to said alternating magnetic field, to a constant magnetic field for a time duration greater than the relaxation time of the rotation of magnetic particles in the liquid resin solvent; said constant magnetic field is applied perpendicular to the direction of said alternating magnetic field and has a field strength greater than the coercivity of the magnetic particles so that in the magnetic coating composition the degree of dispersion is improved;

successively exposiong portions of said magnetic coating composition to said alternating and constant magnetic fields.

6. Method of claim 5 wherein:

each of said portions of said magnetic coating composition are repetitively subjected to said fields.

7. Apparatus for characterizing the degree of magnetic particle dispersion in a magnetic coating composition, said apparatus comprising:

means for generating an alternating magnetic field through said magnetic coating composition;

means for generating for a predetermined time duration a a constant magnetic field perpendicular to said alternating magnetic field in said magnetic coating composition;

said time duration exceeds the relaxation time of the magnetic coating composition;

means for measuring the changes in the magnetic field surrounding said magnetic composition when said constant magnetic field is switched on and off whereby the degree of dispersion of magnetic particles in the coating composition may be characterized from the measured changes.

8. The apparatus of claim 7 and in addition:

a tubular member containing said magnetic coating composition;

said means for measuring comprising:

a measuring coil surrounding said tubular member for sensing changes in the magnetic field surrounding said magnetic composition and generating an induced signal indicative of those changes;

a compensating coil parallel to said measuring coil but separated from said tubular member and connected in electrical opposition to said measuring coil for compensating out the induced signal due directly to the alternating magnetic field.

9. The apparatus of claim 8 and in addition:

said alternating magnetic field is controlled by a function generator, said function generator setting the frequency and amplitude of the alternating magnetic field; and a computer is provided to control and trigger said function generator, to set the field strength and duration of said constant magnetic field, and to evaluate said induced measuring signal.

10. The apparatus of claim 8 and in addition:

means for pumping the coating composition through said tubular member to measure and improve the dispersion grade of the composition.

11. Apparatus of claim 10 and in addition:

coating means for applying said magnetic coating composition to a substrate for producing magnetic record carriers.

* * * * *